(12) United States Patent
Stauber et al.

(10) Patent No.: US 9,182,409 B2
(45) Date of Patent: Nov. 10, 2015

(54) MASS SPECTROMETRY IMAGING METHOD FOR DETECTING AND QUANTIFYING A TARGET MOLECULE IN A TISSUE SAMPLE

(75) Inventors: Jonathan Stauber, Lille (FR); Fabien Pamelard, Armentieres (FR); David Bonnel, Laventie (FR); Grégory Hamm, Lille (FR)

(73) Assignee: IMABIOTECH, Villeneuve D'Ascq (FR)

( * ) Notice: Subject to any disclaimer, the term of this patent is extended or adjusted under 35 U.S.C. 154(b) by 648 days.

(21) Appl. No.: 13/425,570

(22) Filed: Mar. 21, 2012

(65) Prior Publication Data

US 2012/0258485 A1    Oct. 11, 2012

Related U.S. Application Data

(60) Provisional application No. 61/539,681, filed on Sep. 27, 2011.

(30) Foreign Application Priority Data

Mar. 21, 2011    (FR) ..................................... 11 52334

(51) Int. Cl.
  *G01N 24/00*    (2006.01)
  *G01N 33/68*    (2006.01)
  *H01J 49/00*    (2006.01)

(52) U.S. Cl.
  CPC ......... *G01N 33/6851* (2013.01); *H01J 49/0004* (2013.01)

(58) Field of Classification Search
  CPC ..... H01J 49/40; H01J 49/164; H01J 49/0418; H01J 49/0459; H01J 49/0463; H01J 49/004; H01J 49/16; G01N 33/6848; G01N 33/6851; G01N 2560/00; G01N 2500/00; G01N 33/4833; C07K 16/2848; C07K 16/2854
  USPC ............................................. 436/173, 86–90
  See application file for complete search history.

(56) References Cited

FOREIGN PATENT DOCUMENTS

EP          1 580 682      9/2005
WO     WO 2011/073740     6/2011

OTHER PUBLICATIONS

Tech Tip #6 Thermoscientific, "Extinction coefficients", 2008, pp. 1-3.*
Hamm et al. "Quantitative mass spectrometry imaging of propranolol and olanzapine using tissue extinction calculation as normalization factor", J. Proteomics, 2012, v. 75, pp. 4952-4961.*

(Continued)

*Primary Examiner* — Yelena G Gakh
(74) *Attorney, Agent, or Firm* — Saliwanchik, Lloyd & Eisenschenk

(57) ABSTRACT

The invention relates to a method for identifying and quantifying by mass spectrometry imaging at least one target analyte in a tissue sample, comprising the following steps:
  a) depositing the tissue sample to be analyzed on a support;
  b) analyzing the sample by mass spectrometry imaging, so as to obtain the mass spectrum of the target analyte in said tissue sample;
  c) weighting a signal associated with the mass spectrum of the target analyte in said tissue sample by a tissue extinction coefficient (TEC) specific to the target analyte and to the tissue sample which is obtained by using a control tissue sample; and
  d) using the weighted signal of the target analyte to determine the quantity of target analyte in the tissue sample.

20 Claims, 12 Drawing Sheets

(56) References Cited

OTHER PUBLICATIONS

Kaletas, B. K. et al. "Sample preparation issues for tissue imaging by imaging MS" *Proteomics*, 2009, pp. 2622-2633, vol. 9.

Hare, D. et al. "Three-dimensional elemental bio-imaging of Fe, Zn, Cu, Mn and P in a 6-hydroxydopamine lesioned mouse brain" *Metallomics*, Nov. 2010, pp. 745-753, vol. 2, No. 11.

Zabet-Moghaddam, M. et al. "Qualitative and quantitative analysis of lower molecular weight compounds by ultraviolet matrix-assisted laser desorption/ionization mass spectrometry using ionic liquid matrices" *Rapid Communications in Mass Spectrometry*, 2004, pp. 141-148, vol. 18.

* cited by examiner

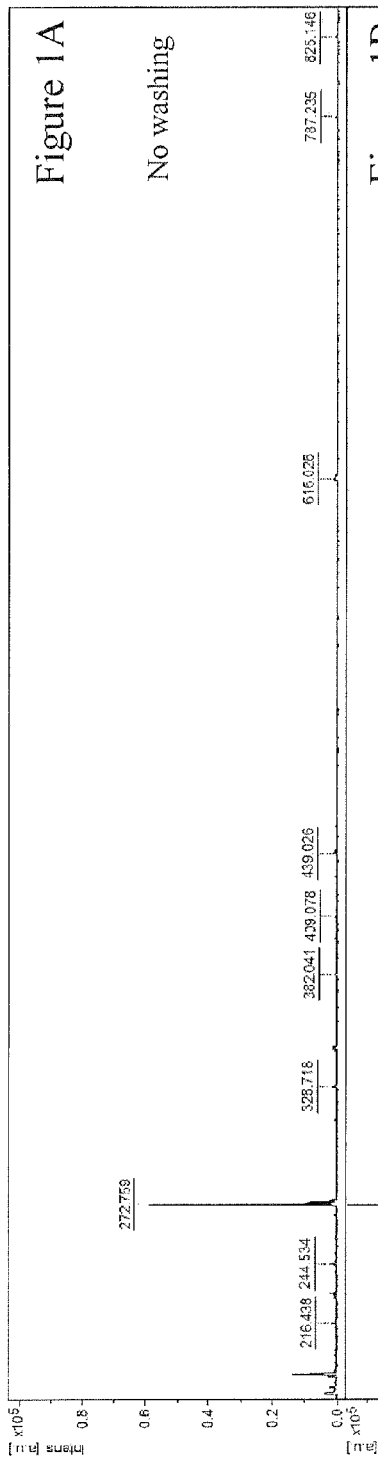
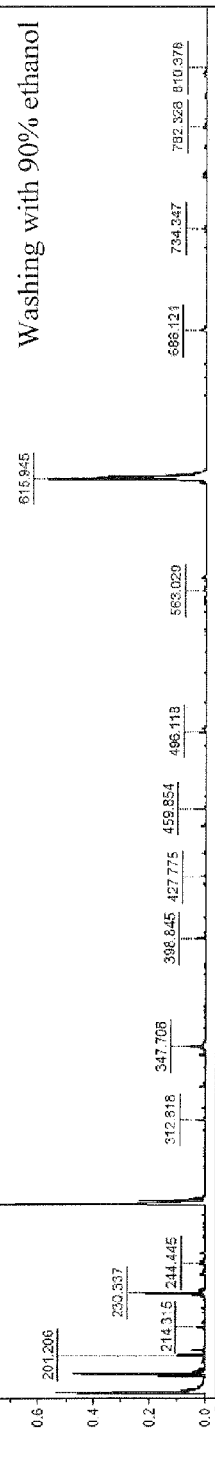
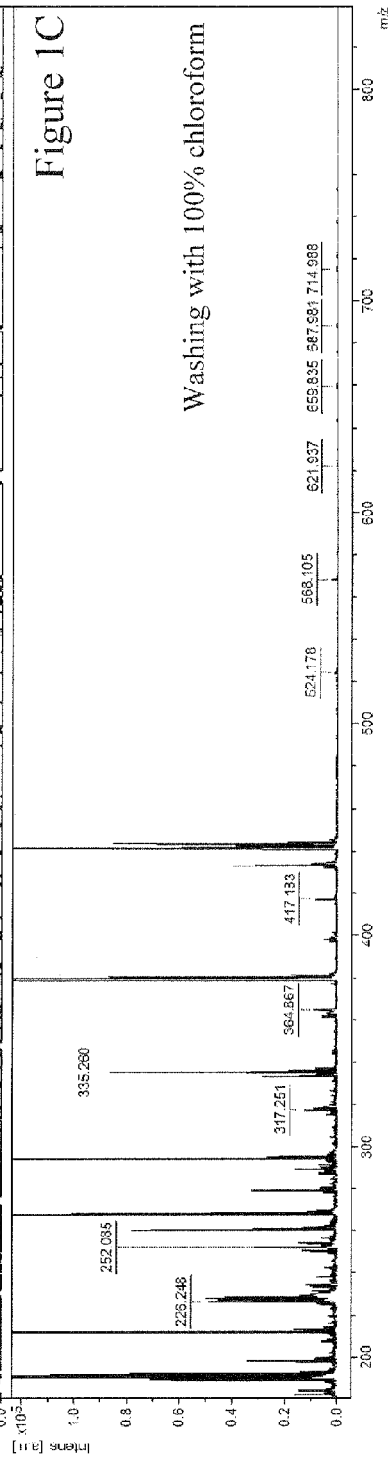
Figure 1A — No washing
Figure 1B — Washing with 90% ethanol
Figure 1C — Washing with 100% chloroform

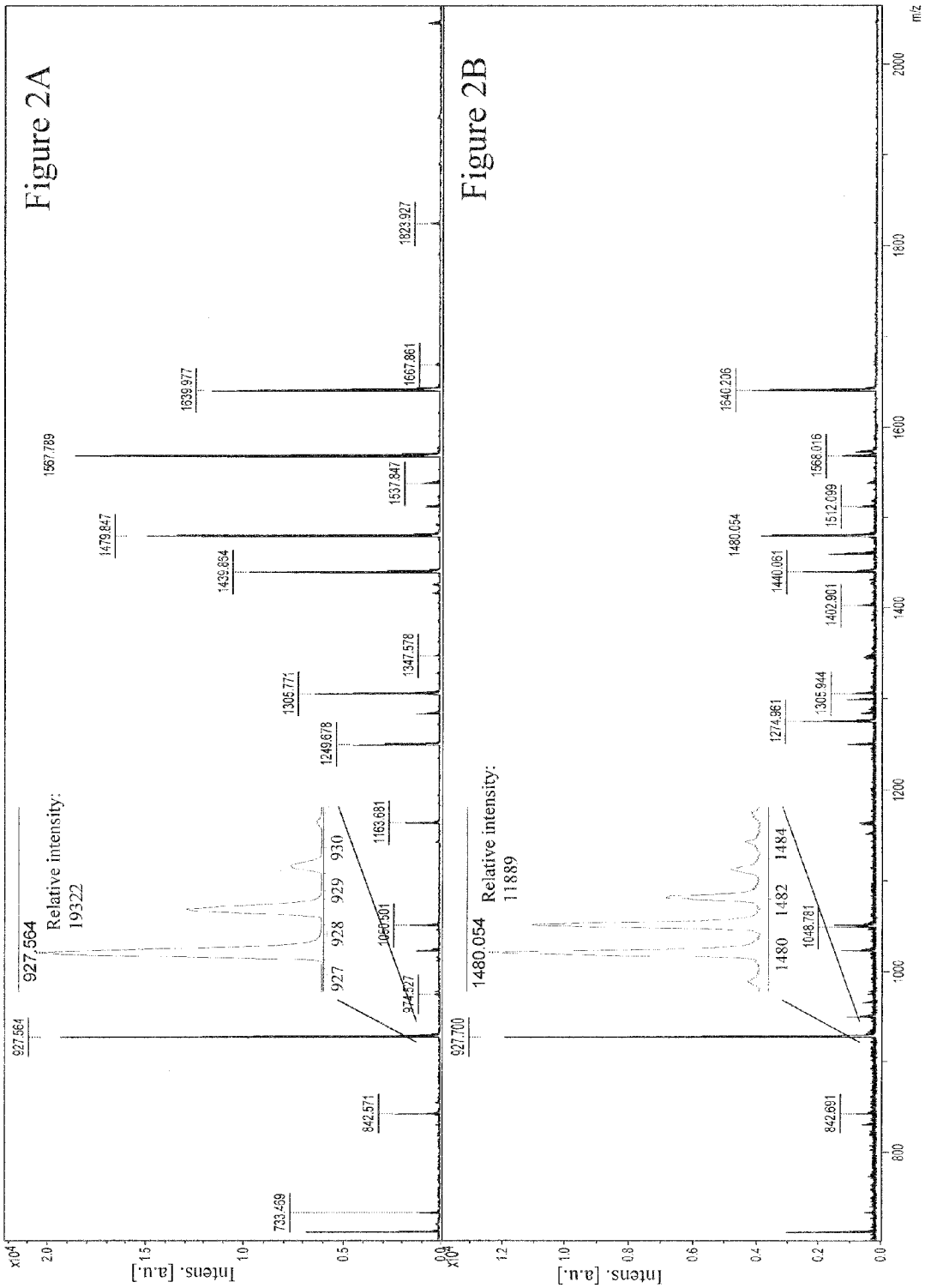

| Intensities | Slide | Brain | Kidney | Lung | Liver | Heart |
|---|---|---|---|---|---|---|
| Mean | 0.6049 | 0.0979 | 0.0473 | 0.0809 | 0.1255 | 0.0760 |
| Standard Deviation | 0.0151 | 0.0095 | 0.0058 | 0.0140 | 0.0239 | 0.0035 |
| % Error | 2.5% | 9.8% | 12.3% | 17.4% | 19.1% | 4.6% |

- 3 pmol/μL
- 640 fmol/μL
- 320 fmol/μL
- 160 fmol/μL
- 80 fmol/μL
- 40 fmol/μL
- 20 fmol/μL
- 0 fmol/μL Define one ROI per concentration spot (here, seven of 4x4 points)

⬇

Calculate the mean intensity of each ROI

| Concentration (fmol/pixel) | 0.0 | 1.5 | 1.3 | 2.8 | 5.7 | 8.9 | 19.4 | 65.2 |
|---|---|---|---|---|---|---|---|---|
| Mean | 0.0011 | 0.0459 | 0.0567 | 0.1498 | 0.2956 | 0.6847 | 0.8251 | 2.0343 |

| Concentration (fmol/pixel) | 0.0 | 1.5 | 1.3 | 2.8 | 5.7 | 8.9 | 19.4 | 65.2 |
|---|---|---|---|---|---|---|---|---|
| Mean | 0.0000 | 0.0074 | 0.0075 | 0.0187 | 0.0481 | 0.1024 | 0.1290 | 0.2785 |

Straight-line equation: $y=0.0042x+0.019$
Correlation coefficient: $R^2=0.933$

| | TEC | Mean intensity per organ | Intensity normalised by the TEC | Correlation with the calibration line (fmol/pixel) | Quantity of target molecule in the organ over the entire area (fmol) | Quantity of target molecule in the organ over the entire area (g) |
|---|---|---|---|---|---|---|
| Brain (172 pixels) | 6.18 | 0,0752 | 0,465 | 106,094 | 19021 (19,02 pmol) | 4.93318E-09 (4,93 ng) |
| Kidney (511 pixels) | 12.8 | 0.00654 | 0.0838 | 15.422 | 7880 (7,88 pmol) | 2.04E-09 (2,04 ng) |
| Lung (253 pixels) | 7.48 | 0.01346 | 0.1007 | 19.454 | 4922 (4,92 pmol) | 1.28E-09 (1,28 ng) |
| Liver (1122 pixels) | 4.82 | 0.00719 | 0.0347 | 3.729 | 4184 (4,18 pmol) | 1.09E-09 (1,09 ng) |
| Heart (328 pixels) | 7.96 | 0.00576 | 0.0458 | 6.386 | 2082 (2,08 pmol) | 5.40E-10 (0,54 ng) | x TEC    [C]=((Int.)-b)/a    x number of pixels    x molar mass (M)

FIGURE 11

MASS SPECTROMETRY IMAGING METHOD FOR DETECTING AND QUANTIFYING A TARGET MOLECULE IN A TISSUE SAMPLE

CROSS-REFERENCE TO RELATED APPLICATION

This application claims the benefit of U.S. Provisional Patent Application 61/539,681, filed Sep. 27, 2011, the disclosure of which is hereby incorporated by reference in its entirety.

FIELD OF THE INVENTION

The invention relates to a method for detecting and quantifying at least one targetmolecule (target analyte) in a sample by mass spectrometry. More particularly, the invention provides a method for detecting and quantifying a target analyte directly on the surface of a sample by using mass spectrometry imaging, in particular matrix-assisted laser desorption/ionization (MALDI) imaging.

Generally, the invention can be applied in any field in which the quantification of a analyte in a sample is useful or necessary. The invention can be applied, for example, in the pharmaceutical field to study the distribution and the pharmacokinetics of a drug in various biological tissues. Additionally, the invention can be applied in the field of agricultural chemistry, notably to evaluate the toxicity and the degradation of a analyte such as a herbicide in plants and/or the environment (soil, surrounding ground water, etc.).

STATE OF THE ART

Mass spectrometry is a technique widely known and used in chemical and biochemical analysis to detect and identify analytes of interest in a sample. Molecular imaging by mass spectrometry, such as MALDI imaging, has been developed in recent years, making it possible to visualize the distribution of analytes of interest directly on sections of biological tissue. MALDI imaging, by virtue of its high sensitivity, makes it possible to simultaneously visualize the distribution of a very large number of different analytes directly on the surface of a sample. In the pharmaceutical field, this technology makes it possible, for example, to compare the distribution of an analyte in various organs at various points of time during treatment.

However, if quantification of the analyte thus detected at time t is desired, it is necessary to couple this imaging technique with quantitative chemical analysis, by a traditional or instrumental method. This second quantification step can be the source of handling and interpretation errors. Moreover, it does not enable direct correlation between the presence of the analyte of interest and its quantitative distribution in the sample.

DESCRIPTION OF THE INVENTION

The invention proposes a method generally using mass spectrometry, during a single analysis, to detect and quantify a target molecule (also referred to as a "target analyte") in a sample. Preferentially, the inventive method uses mass spectrometry imaging, which enables automated acquisition of a signal related to the mass spectrum of the target analyte, directly on the sample, in order to reconstruct images of the distribution and the quantity of said target analyte in the sample.

To this end, according to the invention, an extinction coefficient (TEC) for the target analyte, specific to each target analyte in a given sample, is defined and integrated into the method. Indeed, a given analyte at a given concentration does not emit a signal of the same intensity depending on the sample in which it is detected. Similarly, two different analytes at an identical concentration in a given sample have different signal intensities. Calculation and integration of the TEC make it possible to recognize and to take into account the signal intensity variations associated with the mass spectrum of the target analyte in the sample to be analyzed. The TEC can then be used to normalize the signal obtained for said analyte, so that it is representative of its concentration, independently of the nature of the sample and its location in said sample. Direct quantification of the analyte from the mass spectrometry results obtained for the target analyte in the analyzed sample is thus made possible.

One object of the invention thus relates to a method for identifying and quantifying by mass spectrometry at least one target analyte in a sample, comprising the following steps:
a) depositing the sample to be analyzed on a support;
b) analyzing the sample by mass spectrometry, so as to obtain the mass spectrum of the target analyte in said sample;
c) weighting a signal associated with the mass spectrum of the target analyte in said sample by a extinction coefficient (TEC) specific to the target analyte and to the sample; and
d) using the weighted signal of the target analyte to determine the quantity of target analyte in the sample.

The inventive method can apply to any type of sample that can be analyzed by a mass spectrometer, whether said sample is organic or inorganic. The inventive method is also applicable to any type of support that can be used in mass spectrometry (slide, plate, membrane, etc.). The method is thus particularly suited to the analysis of biological tissues. In this case, tissue sections are prepared, typically on the order of several micrometers thick, and are deposited on a support, such as a slide, enabling their introduction into the mass spectrometer. The inventive method can also be used for the analysis of environmental samples, such as samples of soil, water, plants, etc.

During step a), the sample can be deposited by any known technique, i.e., manually (for example by means of a pipette), or automatically (by using a spotting apparatus, or by spraying or sublimation, for example). The sample can be diluted or treated before deposition on the sample support.

Step b) of analysis of the target analyte can be performed by any mass spectrometry method, notably using direct mass spectrometry (MS) or tandem mass spectrometry (MS", MRM, SRM).

The experimental parameters, such as mass range and/or laser intensity, are advantageously set so as to optimize detection of the target analyte in terms of intensity, sensitivity and resolution.

The mass spectra are then acquired.

For step c), various spectral characteristics can be used as the signal, notably the intensity of the peaks of the mass spectrum, the signal-to-noise ratio (S/N), the area of the peak, etc.

An important step of the method lies in the normalization of the measured signal. To this end, the spectral characteristic selected as the signal for the target analyte in the sample is weighted by an extinction coefficient (TEC) specific to the analyte and to the sample. This weighting normalizes the signal and makes it dependent only on the quantity of the analyte at the origin of the signal.

The (TEC) is representative of the loss or gain in intensity of the target analyte's signal according to the nature of the sample and/or its location on the sample, compared to the signal of said analyte on an inert sample support. The (TEC) is dependent on several factors, notably the sample's origin (animal, plant, bacterium, inorganic), the surface type (tissue, plant cell, metals, etc.), the chemical environment, the presence or absence of chemical treatment of the sample, etc. In the case of a sample of biological tissue, the extinction coefficient of the analyte corresponds to the extinction coefficient of the tissue.

Advantageously, a preliminary histological, chemical or other study of the sample is carried out in order to define various areas of interest and to use them in the calculation of the TEC. Indeed, the TEC can be linked to a specific area of a sample, notably on a heterogeneous sample.

Generally, the TEC is obtained by the following relationship:

$$TEC = \frac{\text{Signal of the target analyte on the support}}{\text{Signal of the target analyte in the control tissue sample}}$$

or inversely:

$$TEC = \frac{\text{Signal of the target analyte in the control tissue sample}}{\text{Signal of the target analyte on the support}}.$$

The signal corresponds to the spectral characteristic of the mass spectrum of the target analyte selected, for example the intensity of the peak of said analyte obtained on the mass spectrometer. Of course, the spectral characteristic used for the analyte in the reference medium and on the sample must be the same.

The TEC is calculated using the same concentration of the target analyte in a reference medium and on the sample which is to be analyzed. It is also possible to use, in the place of the target analyte in a reference medium, an analyte that has similar physicochemical properties to those of the target analyte (e.g. an isotopically labeled target analyte).

For the calculation of the TEC, the reference medium corresponds advantageously to the sample support alone. To this end, for example, the analyte is solubilized in a suitable medium (organic solvent, water or other) before deposition on the sample support. Deposition is followed by evaporation of the solvent, so that a dry deposition of the analyte on said support is obtained. It is the signal obtained for said analyte on the sample support that is then used for the TEC.

The TEC value is generally the mean of several measurements of the target analyte under the same conditions, in order to obtain a reliable coefficient.

Preferentially, the target analyte extinction coefficient (TEC) is calculated only once for a given target analyte in a given type of sample, and is reused for each analysis of said target analyte in the given type of sample. Thus, a database of TECs, listing the TEC of a target analyte in several different samples, can advantageously be created for a given target analyte, and used in each analysis of said analyte in various samples.

Alternatively, the TEC value can be determined prior to each analysis.

During step d), the weighted signal measured in the sample is used to quantify said analyte. Indeed, the value of the weighted signal only depends on the concentration of the analyte. It is thus possible, for example, to determine the quantity of the target analyte by referring to a reference signal for the target analyte.

The expression "reference signal for the target analyte" refers to a signal representative of a known concentration, independent of the nature of the sample and its position in the sample. The reference signal can be a mean or median value (or a range of mean or median values) determined or established beforehand for a known quantity of a given analyte. It can also be a standard curve.

According to the method selected and, if need be, to the reference signal used, it is possible to determine the quantity of target analyte in a relative or absolute manner.

For example, the reference signal is obtained by preparing a standard range with at least three different known concentrations of the target analyte (or of another analyte with physicochemical properties similar to those of the target analyte), in a reference medium such as a sample support on which the solubilized analyte has been deposited. If the analyte is deposited on a tissue sample, the analyte is advantageously adsorbed on said tissue after deposition and evaporation of the solubilization medium.

An internal standard, different than the target analyte, can be introduced into the standard range in order to normalize the signal of said target analyte. The analyte used as internal standard advantageously has physicochemical properties similar to those of the target analyte. A constant concentration of this standard is added to the standard range of the target analyte before deposition.

Next, the mass spectrum for each concentration is analyzed. The spectral characteristic chosen as the comparison signal is read for each of said concentrations. Advantageously, after obtaining the mass spectra for each concentration point, the selected associated spectral characteristic can be used to establish a calibration curve for said analyte. It is then sufficient to refer to this calibration curve to determine precisely the concentration in the analyzed sample.

When the inventive method uses a mass spectrometry imaging technique requiring the use of a matrix, such as MALDI or matrix-enhanced secondary ion mass spectrometry (ME-SIMS) imaging, it is possible to use a standard analyte to obtain the reference signal of the target analyte.

For example, a standard analyte, of known molecular weight and at a known concentration, can be added to the MALDI matrix before use. The resulting mixture is then deposited on the sample to be analyzed and on the support before analysis step b). The signal obtained for the standard analyte corresponds to the reference signal for the target analyte. By comparing the signal of the target analyte with the reference signal, the relative quantity of target analyte in the sample can be deduced.

The standard analyte is any analyte whose molecular weight is known. Preferentially, a analyte with a molecular weight much different than the molecular weight of the target analyte is used as the standard analyte, so that the mass spectra obtained can be easily analyzed. The concentration of the standard analyte, taken up in a solubilization solution (aqueous or containing a solvent), is defined in order not to saturate the total signal.

The matrix/standard analyte mixture is deposited uniformly on the sample as well as on the periphery of the sample, i.e., on the sample support, to enable calculation of the TEC. During drying, co-crystallization of the mixture can be observed with the naked eye.

The signal obtained for the standard analyte, whose concentration is known, is used to normalize the spectral characteristics of the target analyte in order to enable its quantification. It is thus also possible to take into account the effect of the matrix, described in further detail below.

Another possibility for obtaining a reference signal (or internal standard) is to use a deuterated analyte, i.e., a analyte labeled with deuterium, or a analyte labeled with any other suitable isotope, as the standard analyte.

For example, before analysis step b), a known concentration of the target analyte labeled with deuterium atoms can be added to the sample to be analyzed. If a matrix is used, the deuterated analyte can be mixed with the matrix. The resulting mixture is advantageously homogenized before being deposited uniformly on the sample and the sample support. Otherwise, a solution containing the deuterated analyte can be deposited on the sample.

The target analyte and its deuterated complement can then be evaluated simultaneously on the analyzed sample. Considering that their ionization will be identical, their analysis by mass spectrometry will result in the same signal with a difference in mass due to the presence of deuterium. The signal obtained for the deuterated analyte corresponds to the reference signal for the target analyte. Since the concentration of the deuterated analyte is known, the ratio can then be calculated to yield a relative quantity.

The inventive method can advantageously be used with mass spectrometry imaging. In this case, it is possible to use various ionization sources such as MALDI, laser desorption/ionization (LDI), desorption electrospray ionization (DESI), etc., combined with various types of analyzers such as time-of-flight (TOF), orbitrap, Fourier transform ion cyclotron resonance (FT-ICR), etc. This imaging technique makes it possible to quantify the target analyte directly on the ion density map obtained for the sample, corresponding to the spatial distribution of the target analyte in said sample. The weighted signal on said ion density map can indeed be compared with a specific reference signal of the analyte of interest.

Certain mass spectrometry imaging techniques, such as MALDI or ME-SIMS, require the sample to be analyzed to be covered beforehand by a matrix comprising small UV-absorbing organic molecules. This matrix enables the desorption and the ionization of the molecules present on the sample.

The inventive method can be used regardless of the matrix chosen. These matrices are provided in solid form (crystallization on the sample) or liquid form and are ionic or nonionic. The matrix is chosen according to the mass range analyzed. They are generally prepared immediately before use in a solvent/aqueous solution mixture.

Several methods for depositing the matrix are possible, notably manual deposition using a pipette, which makes it possible to deposit a precise volume of matrix directly on the sample. It is also possible to deposit the matrix by spraying or by nebulization, wherein the matrix is sprayed or nebulized directly on the tissue by a robotic system or manually. Similarly, deposition by microdroplets wherein the matrix is spotted on the sample via piezoelectric, acoustic or syringe pump systems can be envisaged. It is also possible to deposit the matrix by sifting, in order to deposit the matrix in solid form.

Advantageously, if the inventive method uses MALDI mass spectrometry imaging, a step of evaluating the homogeneity of the deposition of matrix on the sample can be expected. Indeed, the signal corresponding to the matrix used can indicate the quality/uniformity of the deposition of said matrix. Matrix defects on the surface of the sample can then be correlated with the lack of detection or the loss of intensity of the signal of the target analyte in the sample studied.

The homogeneity of the matrix can be evaluated according to qualitative criteria by observing under an optical microscope the homogeneity of the deposition on the surface of the sample, and/or according to quantitative criteria by monitoring variations in the signal relative to the matrix itself on the sample.

With regard to qualitative criteria, it must be ensured that the matrix has been deposited as uniformly as possible on the surface under study and that there are no areas void of matrix and that its crystallization is optimal.

For quantitative evaluation of the homogeneity of the matrix deposition, the matrix is considered as an analyte itself whose signal during sample analysis is detected in the same way as the signal of the target analyte. The signal of the matrix molecule is then compared with its reference signal. The reference signal of the matrix corresponds in this case to the signal emitted by the matrix on a deposition of reference matrix, i.e., on a sample and on a sample support used specifically to measure the reference signal of the matrix.

By these additional steps, the signal of the target analyte is validated and normalized to take into account variation in the quality of the matrix deposition, which can affect the matrix deposition's spectral characteristics.

This consideration of the matrix effect can be particularly advantageous when the monitoring of changes in the presence of a target analyte over time is desired, since matrix deposition quality can vary from one sample to the next.

The inventive method can be used to analyze any kind of molecule (target analyte), such as, for example, peptides, polypeptides, proteins, amino acids, nucleic acids, lipids, metabolites, etc., and, in general, any analyte that is active pharmaceutically or otherwise and that can be ionized by mass spectrometry. The inventive method is particularly advantageous for the analysis of small analytes (notably drugs), i.e., analytes of molecular weight less than 2000 Da.

If the target analyte is a protein of high molecular weight, it is possible to enzymatically and/or chemically pretreat the target analyte in order to cleave it into several peptides (FIG. 2). Detection and quantification are then carried out for at least one of the peptides resulting from the enzymatic digestion and/or the chemical degradation/modification, representative of said protein. For example, trypsin can be used as an enzyme to cleave the target protein into several peptides identified beforehand. Chemical pretreatment can consist of chemical hydrolysis, by acids or bases, a Maillard reaction, the formation of isopeptides or lysinoalanine, etc.

Similarly, it is possible to treat the sample to be analyzed with at least one solvent and/or at least one detergent prior to detection step b) so as to optimize detection of the target analyte. For example, washing with chloroform (FIG. 1-*a*) removes certain classes of lipids. Washing with ethanol (FIG. 1-*b*) enables better detection of low-mass analytes. These two washings, in the experiment illustrated in FIG. 1, remove certain analytes, in particular lipids, thus promoting the detection of new ions directly on the tissue.

The inventive method can also be used to detect and quantify at least two different target analytes on the same sample, simultaneously or sequentially.

The inventive method is particularly suited to the detection and quantification of target analytes on a section of biological, plant or animal tissue. Notably, analysis on a section of whole animal can make it possible to compare, on the same sample, the distribution of target analytes in various tissues of said animal.

According to the invention, the source data, i.e., the TEC of the target analyte and the matrix effect, can be normalized with a view to quantification by means of a computer program that integrates all or part of these factors. This computer program, or data analysis software, advantageously uses the TEC value weighted, if need be, by the matrix effect during the processing of the image in the case of mass spectrometry imaging.

Another object of the invention thus relates to a computer-readable data medium comprising computer-executable instructions, such as, for example, the reading of raw data resulting from mass spectrometry analysis, and/or determination of TECs and/or determination of the calibration curve, and/or normalization of the raw data using said TECs or said calibration curve in order to obtain a quantitative value for the target analyte. Advantageously, these computer-executable instructions are suited to enable a computer system to execute at least step c) of the inventive method.

The data medium advantageously comprises at least one TEC database for at least one target analyte in at least two different sample types. Preferentially, in the case of biological samples, such as a section of whole animal, the database lists the TECs of at least one target analyte in various tissues of said sample.

The data medium can also comprise a database of the reference signal of at least one matrix used in mass spectrometry imaging. Thus, by using an imaging method that makes use of the data medium, it is possible to take into account the matrix effect during the analysis of the sample.

BRIEF DESCRIPTION OF THE FIGURES

FIGS. 1A-1C. Examples of the effect of two washings in direct analysis by mass spectrometry of heart tissue. (a): Signal obtained from heart tissue without any preliminary washing of the matrix deposition. (b): Signal obtained from heart tissue on a section adjacent to (a) using a 90% ethanol washing prior to deposition of the matrix. (c): Signal obtained from stomach tissue on a section adjacent to (a) using a 100% chloroform washing prior to deposition of the matrix.

FIGS. 2A-2B. MALDI-TOF mass spectrum of a digested model protein (bovine serum albumin with trypsin as digestion enzyme) on (a) a reference support (slide) and (b) tissue (rat liver). Example of the m/z 928 fragment (YLYEIAR): observation of the extinction of the mass signals relative to the peptide on the tissue, with the TEC equal to 1.62.

FIG. 5A: Optical image of the kidney, delimitation of several regions of interest (ROI) or areas of points of equal dimensions within the target organ. FIG. 5B: Table of mean intensities of the internal standard by ROI and between ROI (ROI mean).

FIG. 6A: Table summarizing propranolol intensities by organ or by target areas. FIG. 6B: Histogram of propranolol intensities by organ or by target areas.

FIG. 7A: Mathematical relationship: Table summarizing TECs calculated for propranolol by target organ. FIG. 7B: Histogram of TECs calculated for propranolol by target organ.

FIG. 8A: Optical image of standard range depositions. FIG. 8B: Mass spectrometry image of the standard range, distribution of the target analyte. FIG. 8C: Table summarizing mean intensities of ROI of the standard range of the target analyte.

FIG. 9A: Table summarizing mean intensities of ROI of the standard range of the target analyte. FIG. 9B: Graph of the calibration line. FIG. 9C: Correlation coefficient and straight-line equation.

FIG. 10A: Optical image of a sagittal section of mice at 20 min post-injection of the target analyte and visualization of various organs or target areas (2-brain, 3-kidney, 4-lung, 5-liver, 6-heart). FIG. 10B: Mass spectrometry image of the distribution at t=60 min post-injection of the target analyte ($[M+H]^+$ ion at m/z 260) by intensity. FIG. 10C: Mass spectrometry image of the distribution at t=20 min post-injection of the target analyte after normalization by the TEC and correlation with the calibration line, access to the quantity per unit of area of the target analyte.

FIG. 11. Quantification on the MS image of the target analyte, table summarizing the quantity of target analyte in the various organs. Explanation of the methodology for calculating the latter from mean intensities by organ and pixel with use of the TEC.

FIG. 12A: Optical image of a sagittal section of control mouse kidney. FIG. 12B: Mass spectrometry image of the distribution of the internal standard (olanzapine, $[M+H]^+$ ion at m/z 313.3) mixed with the matrix on and apart from the sample and intensity scale. FIG. 12C: Histogram of the TEC calculated for olanzapine in the kidney.

FIG. 13A: Mass spectrometry image of the standard range, distribution of the target analyte. FIG. 13B: Presentation of the calibration line relative to the MS image of olanzapine, its equation, its correlation coefficient and its limits of detection and of quantification in fmol/mm$^2$.

FIG. 14A: Optical image of a sagittal section of mouse kidney at 2 hours post-administration of the target analyte. FIG. 14B: Mass spectrometry image of the distribution at t=2 h post-administration of the target analyte ($[M+H]^+$ ion at m/z 313.3) by intensity.

EXAMPLES

Figure 3:
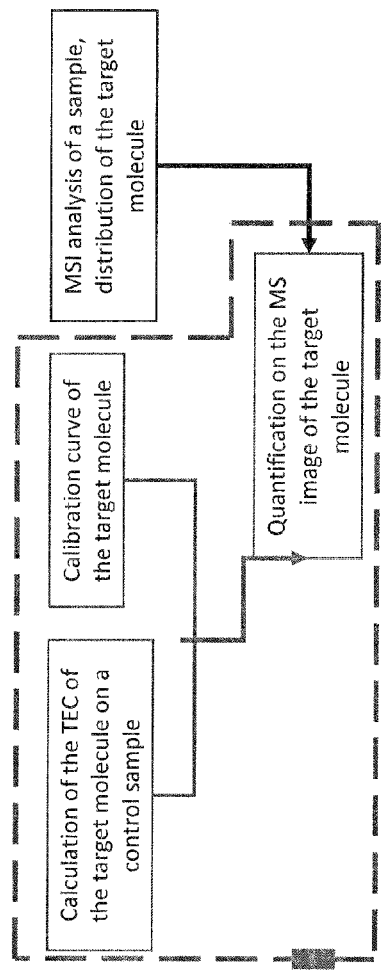
FIG. 3. A schematic representation of the principal steps of the inventive method, according to an example of implementation using mass spectrometry imaging.
Figure 4:
FIGS. 4A-4B. Methodology for calculating the tissue extinction coefficient in the study of the distribution of propranolol in whole-body mouse. (a) Optical image of a sagittal section of control mouse for visualizing various organs or target areas (1-slide alone, 2-brain, 3-kidney, 4-lung, 5-liver, 6-heart). (b) Mass spectrometry image of the distribution of the internal standard (propranolol, $[M+H]^+$ ion at m/z 260) mixed with the matrix on and apart from the sample and intensity scale.

The inventive method will now be described in further detail using specific examples and the figures presented above. These examples are given for illustrative purposes only and by no means restrict the scope of the invention.

Example 1

In example 1, the distribution of a drug (propranolol) in various organs of a mouse is studied by MALDI mass spectrometry imaging. Of course, in an almost identical manner an imaging device other that MALDI could be used, such as, for example, the following sources: SIMS, DESI, DIOS, ICP, MALDI microscope, SNOM, SMALDI, LA-ICP, ESI (liquid extraction on tissue), MILDI, JEDI, ELDI, etc.

Materials and Methods

Materials:

2,5-Dihydroxybenzoic acid (DHB) (Sigma-Aldrich, Saint-Quentin Fallavier, France)

Trifluoroacetic acid (TFA) (Sigma-Aldrich)

Methanol (Sigma-Aldrich)

Propranolol (Sigma-Aldrich)

Animals:

Male Swiss mice weighing 25-40 g (Charles River, France) were used. Propranolol taken up in 0.9% NaCl solution was injected by intravenous route at a concentration of 7.5 mg/kg.

The animals were sacrificed by $CO_2$ asphyxiation at 20 minutes post-injection.

The animals were then plunged into 100% isopentane solution cooled by liquid nitrogen for rapid freezing.

The animals were then stored at −80° C.

Preparation of samples for mass spectrometry:

The samples (control and dosed tissue) were sectioned into 20 μm-thick layers using a CM1510S cryostat (Leica Microsystems, Nanterre, France) cooled at −26° C. The sections were then deposited on conductive ITO (indium tin oxide) slides (Bruker Daltonics, Bremen, Germany).

Finally, the sections were placed in a desiccator for 20 minutes.

Preparation for acquisition by MALDI imaging:

A DHB matrix was used for the analysis of the target analyte (propranolol) in the dosed tissue sections. This matrix was prepared at a concentration of 40 mg/ml in methanol/0.1% TFA (1:1, v/v). The matrix solution was deposited using the SunCollect spraying system (SunChrome, Germany).

On the same slide but apart from the dosed tissue section, a range of dilutions of propranolol taken up in water was deposited manually using a pipette (1 μl per point) prior to deposition of the matrix. This range of dilutions extends from 10 pmol/μl to 0.02 pmol/μl and includes seven points.

Preparation for calculation of the TEC:

On a control tissue section, a 10 mg/ml HCCA matrix solution in ACN/0.1% TFA (7:3, v/v) was also prepared, to which a 10 pmol/μl propranolol solution was added. The matrix solution was deposited using the SunCollect spraying system (SunChrome, Germany) to cover the surface of the control tissue section.

MALDI image acquisition:

The images were obtained using an AutoFlex Speed MALDI-TOF mass spectrometer (Bruker Daltonics, Bremen, Germany) equipped with a Smartbeam laser. The data was generated in positive reflectron mode. A total of 700 spectra were obtained for each spot with a 1000 Hz laser frequency and a 300×300 μm' image spatial resolution on a mass range of 100 Da to 1000 Da. The FlexImaging version 2.1 software was used to reconstruct the images.

1-Calculation of the TEC of the Target Analyte (Propranolol) on a Control Sample A sagittal section of the whole animal, prepared as specified above and used as a control sample, is deposited on a slide.

The propranolol solution used as an internal standard is mixed with the matrix above, prior to deposition of the resulting mixture on the control sample.

The control sample is then analyzed by mass spectrometry imaging in order to obtain an image of the distribution of the internal standard on the control sample and on the support slide (FIG. 3B).

The various organs of interest can advantageously be located beforehand by optical imaging of the control sample (FIG. 3A).

Several regions of interest (ROI) of equal dimensions for each organ on the slide are then delimited on the mass spectrometry image of the control sample. The intensity of the peaks of the mass spectrum was selected as the reference signal. The mean intensities of the internal standard for each ROI and each organ of interest were recorded. For each organ, a mean intensity (ROI mean) was calculated from the intensity obtained for all the corresponding ROI. This mean ROI will be used to calculate the extinction coefficient of propranolol in each organ studied.

Figures 5A, 5B:
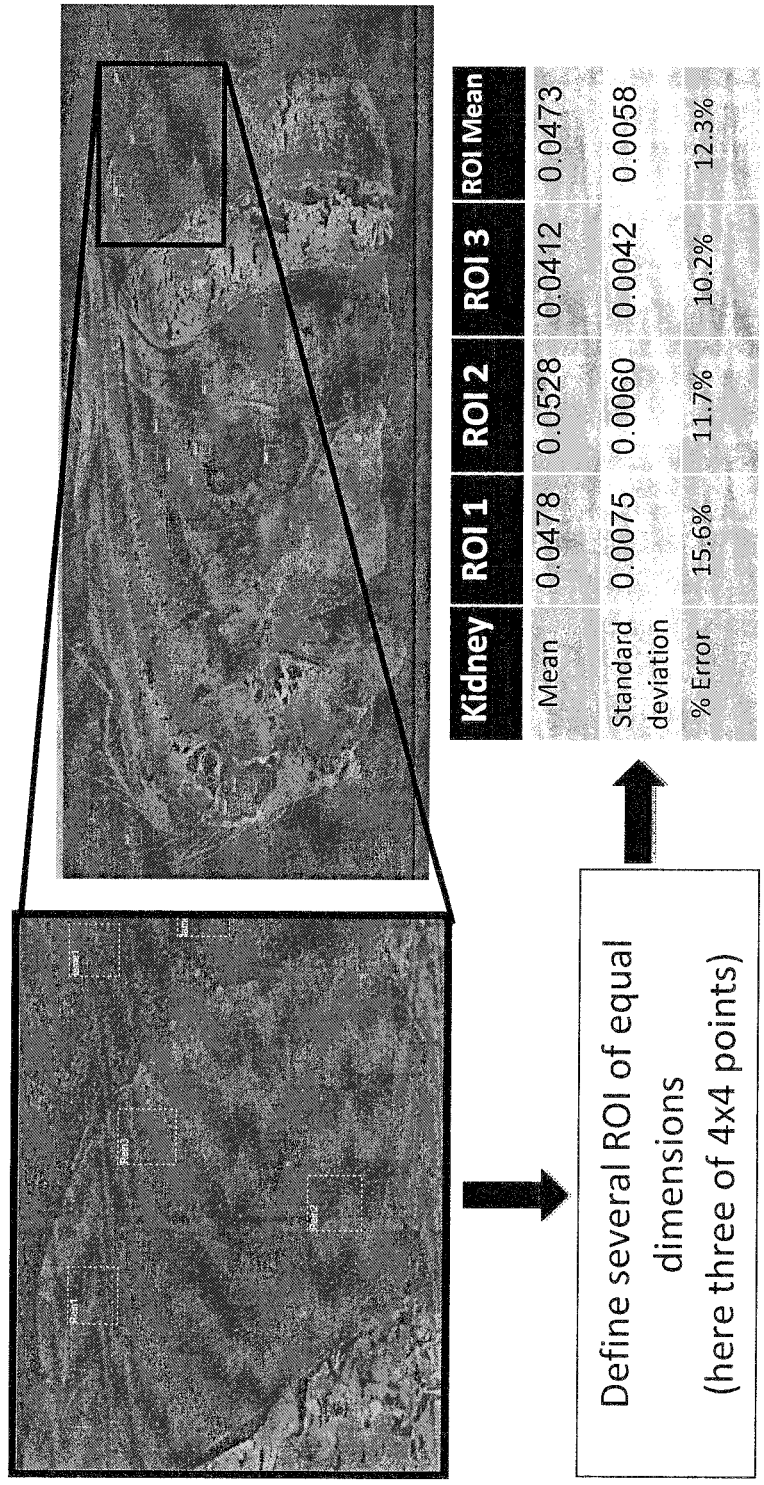
FIGS. 5A-5B. Methodology for calculating the tissue extinction coefficient of propranolol in the kidney.

FIG. 5 shows a schematic diagram of these various steps for the kidney.

Figures 6A, 6B:
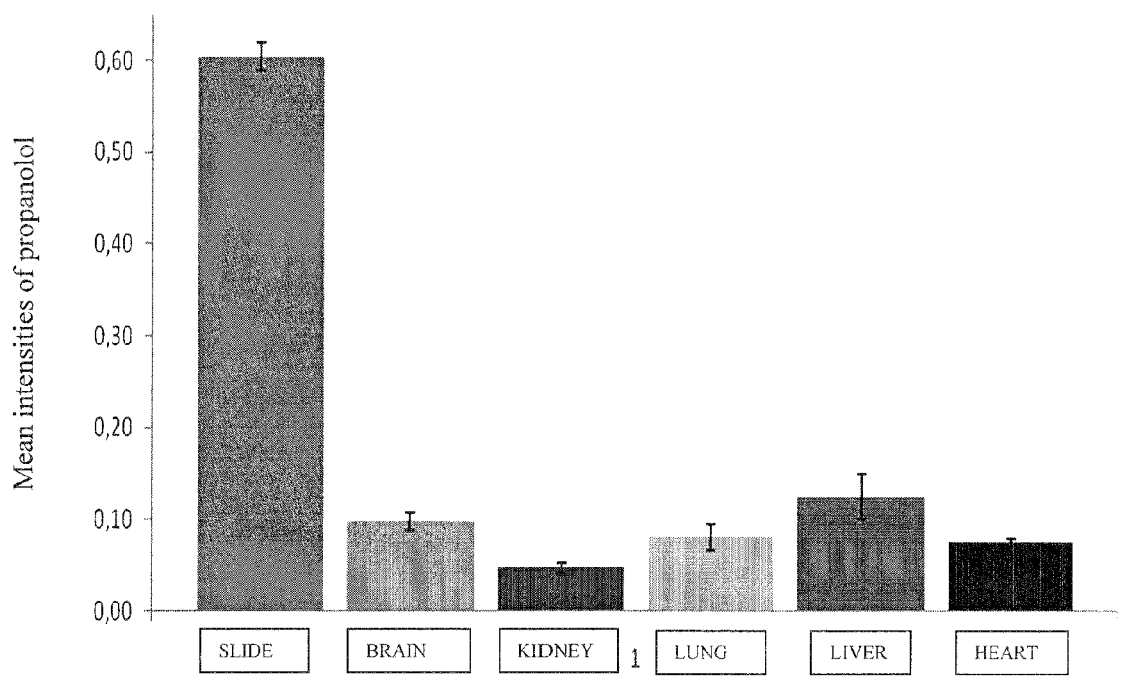
FIGS. 6A-6B.

FIG. 6A summarizes the mean ROI obtained for propranolol in the various organs of interest of the control sample, and FIG. 6B shows the histogram of the corresponding signal intensities obtained.

Figures 7A, 7B:
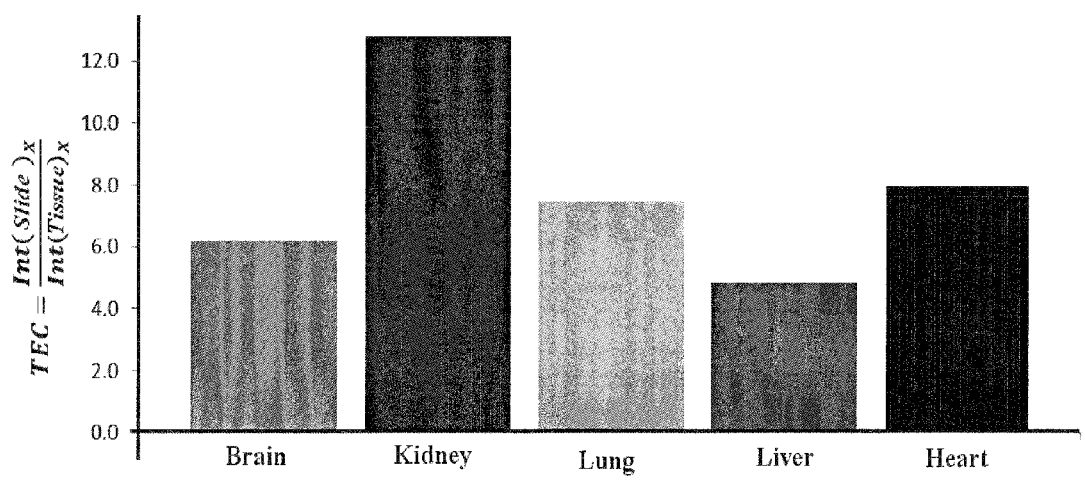
FIGS. 7A-7B. Calculation of the tissue extinction coefficient.

The TEC can then be calculated (FIG. 7A) using the mean ROI values from the slide and from each organ, according to the mathematical formula:

$$TEC = \frac{Int(\text{slide})_x}{Int(\text{tissue})_x}$$

Thus, for the same concentration of propranolol, the associated signal in the kidney is divided by nearly 13 compared to the expected signal, i.e., the signal on the slide. On the other hand, the signal is only divided by 4.82 in the liver and 7.96 in the heart. The signal is divided by less than 8 in the lungs and by 6.18 in the brain.

2-Propranolol Calibration Curve

Figures 8A, 8B, 8C, 9A, 9C:
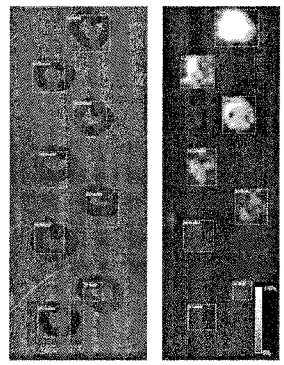
FIGS. 8A-8C: Determination of the calibration curve for the target analyte.
FIGS. 9A-9C.
Figure 9B:
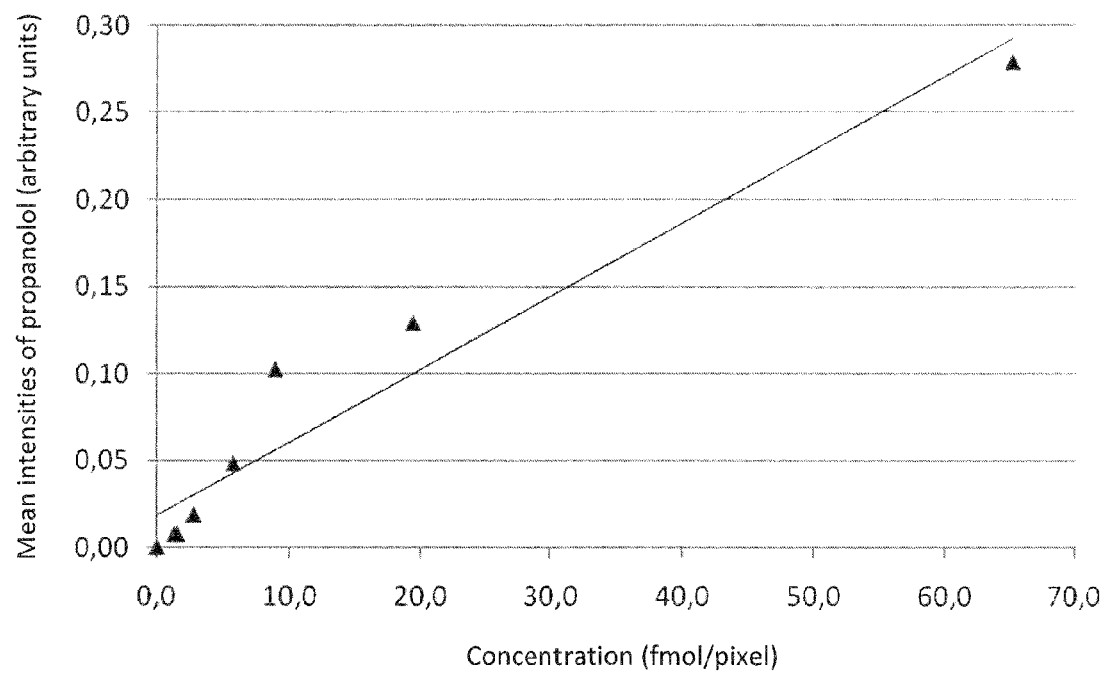

In the example described herein using FIGS. 8 and 9, the reference signal for the target analyte (propranolol) corresponds to the signal obtained for a standard range of seven concentrations of propranolol.

Seven droplets of a propranolol and matrix solution, corresponding to seven different concentrations of propranolol (0 to 3 pmol/μl), are manually deposited on a slide using a pipette and allowed to dry. To make it easier to read the results, the droplets are deposited in increasing concentrations and sufficiently spaced to avoid any risk of overlapping.

The mass spectrometry image obtained for these various concentrations (FIG. 8B) is normalized for all points in the range using an ROI of identical dimensions, from which a mean reference intensity, or reference signal, for propranolol is defined. A calibration line (FIG. 9B) can then be plotted, thereafter making it possible during analysis to correlate any signal intensity obtained for propranolol with a concentration by pixel.

Figure 10A:
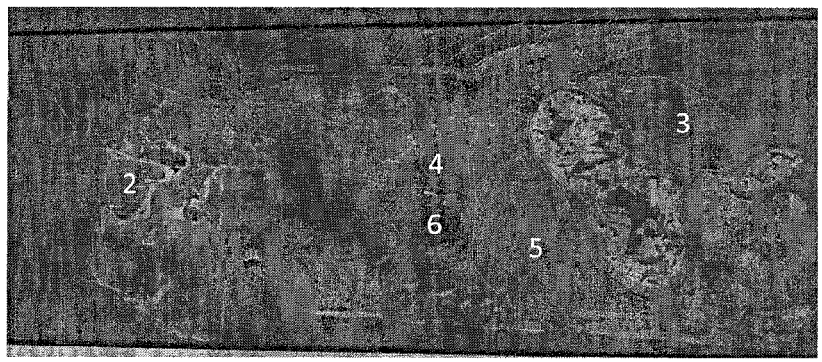
FIGS. 10A-10C. Quantification on the mass spectrometry image of the target analyte (propranolol), in a whole body.
Figure 10B:

3-Quantification of Propranolol Directly on the Mass Spectrometry Image of the Sample A sagittal section of the whole animal, prepared as specified above and if possible in the same plane as the section used as the control sample during the calculation of the TEC, is deposited on a slide in order to perform an analysis by mass spectrometry imaging (FIG. 10B).

The signal intensity obtained for propranolol is increased in each organ of interest as a function of the TEC calculated for each.

Figure 10C:
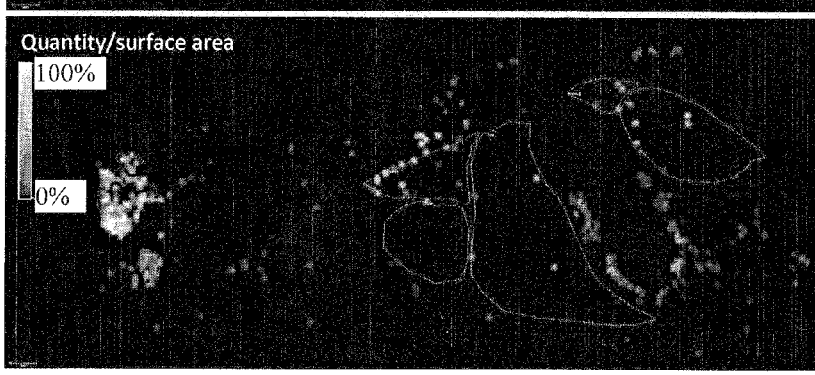

A mass spectrometry image of the section of the whole animal is obtained in which signal intensity corresponds to absolute intensity, i.e., intensity of the propranolol concentration alone (FIG. 10C). This image can be correlated with the calibration line previously calculated for propranolol in order to determine the quantity of propranolol in the sample directly by visualizing the image.

Thus, in the example described herein, it is noted that propranolol is virtually absent from the liver and lungs, in contrast to the brain where the distribution of propranolol is greatest with a total quantity of the target analyte of about 5 ng. Propranolol is also observed in the kidneys and lungs, with quantities ranging from 1.28 ng to 2 ng.

Example 2

In the second example, the distribution of another drug (olanzapine) in the kidneys of a mouse is studied by MALDI mass spectrometry imaging. Any other imaging device could be used in a virtually identical manner.

Materials and Methods
Materials:
Hydroxycinnamic acid (HCCA) (Sigma-Aldrich, Saint-Quentin Fallavier, France),
Trifluoroacetic acid (TFA) (Sigma-Aldrich)
Acetonitrile, DMSO, water (Sigma-Aldrich)
Olanzapine (Lilly Research Laboratories, Eli Lilly and Co., Indianapolis, Ind.)
Animals:
Male Swiss mice weighing 25-40 g (Charles River, France) were used. Olanzapine was administered orally at a concentration of 8 mg/kg.

The animals were sacrificed by $CO_2$ asphyxiation at 2 hours post-administration.

The animals were then plunged into 100% isopentane solution cooled by liquid nitrogen for rapid freezing.

The animals were then stored at −80° C.

Preparation of samples for mass spectrometry:
The samples were sectioned into 10 μm-thick layers under conditions identical to those of example 1 above.

Preparation for acquisition by MALDI imaging:
An HCCA matrix was used for the analysis of the target analyte (olanzapine) in the tissue sections. This matrix was prepared at a concentration of 10 mg/ml in ACN/0.1% TFA (7:3, v/v). The matrix solution was deposited using the SunCollect spraying system.

On the same slide but apart from the tissue section, a range of dilutions of olanzapine taken up in DMSO was deposited manually using a pipette (1 μl per point) prior to deposition of the matrix. This range of dilution extends from 60 pmol/μl to 1 pmol/μl and includes seven points.

Preparation for calculation of the TEC:
On a control tissue section adjacent to that used for MALDI image acquisition, a 10 mg/ml HCCA matrix solution in ACN/0.1% TFA (7:3, v/v) was also prepared, to which a 10 pmol/μl olanzapine solution was added. The matrix solution was deposited using the SunCollect spraying system to cover the surface of the tissue section.

MALDI image acquisition:
The images were obtained in a manner identical to example 1, but with a 200×200 μm² image spatial resolution.

1-Calculation of the TEC of the Target Analyte (Olanzapine) on a Control Sample

A control sagittal section of kidney, prepared as specified above and used as a control sample, is deposited on a slide. The olanzapine solution used as an internal standard is mixed with the matrix above, prior to deposition of the resulting mixture on the control sample.

Figure 12C:
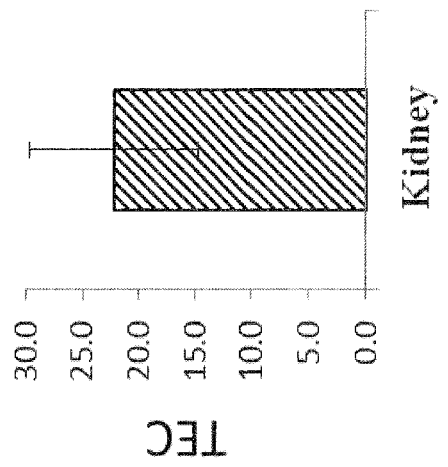
FIGS. 12A-12C. Methodology for calculating the tissue extinction coefficient of olanzapine in the kidney.
Figure 12A:
Figure 12B:
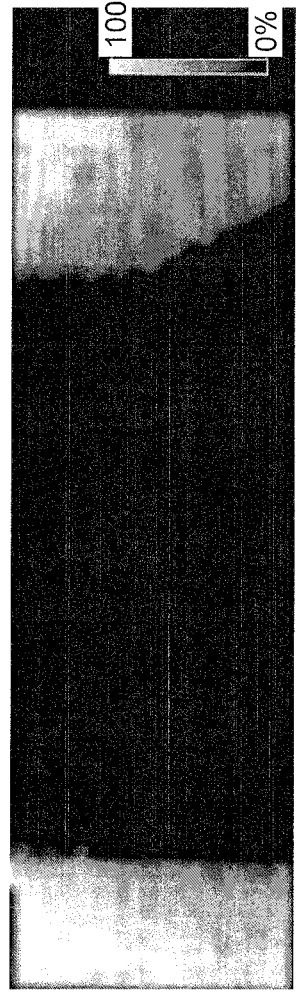

The control sample is then analyzed by mass spectrometry imaging in order to obtain an image of the distribution of the internal standard on the control sample and on the support slide (FIG. 12B). The optical image of the control sample presented in FIG. 12A makes it possible to visualize the organ of interest, i.e., the kidney.

Several regions of interest (ROI) of equal dimensions on the kidney and on the slide are then delimited on the mass spectrometry image of the control sample. The intensity of the peaks of the mass spectrum was selected as the reference signal. The mean intensity (ROI mean) is calculated as for example 1. This mean ROI will be used to calculate the extinction coefficient of olanzapine in the kidney.

The TEC (FIG. 12C) is calculated according to same methodology as example 1. It is thus observed that, for the same concentration of olanzapine, the associated signal in the kidney is divided by nearly 22.2 compared to the expected signal, i.e., the signal on the slide.

2-Olanzapine Calibration Curve

Figure 13A:
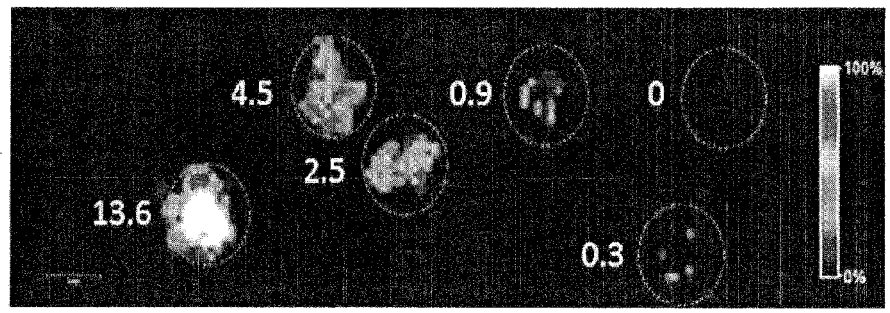
FIGS. 13A-13B. Determination of the calibration curve for the target analyte.
Figure 13B:
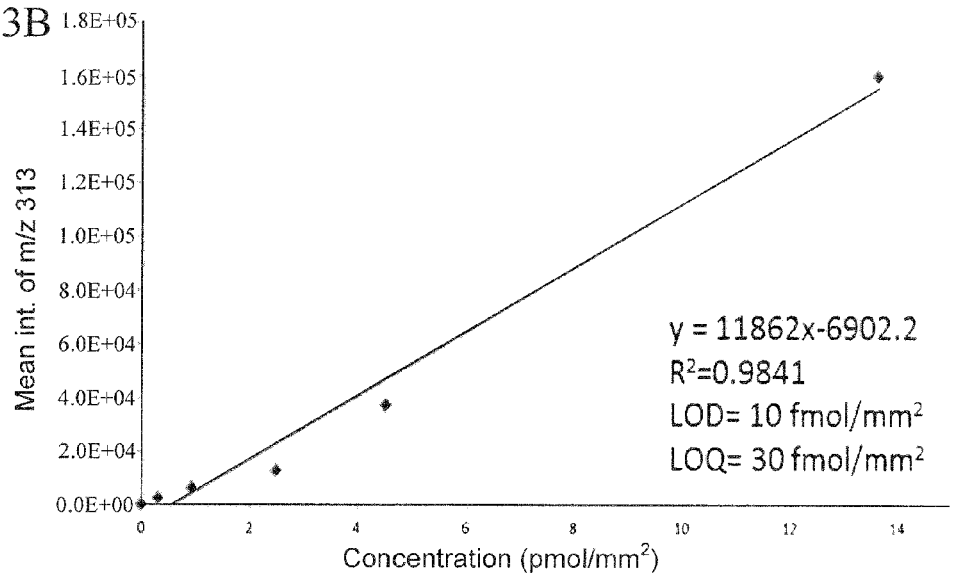

The reference signal for olanzapine, represented in FIG. 13, corresponds to the signal obtained for a standard range of seven concentrations of olanzapine.

Seven droplets of a olanzapine and matrix solution, corresponding to seven different concentrations of olanzapine (0 to 60 pmol/μl), are manually deposited on a slide using a pipette and allowed to dry. To make it easier to read the results, the droplets are deposited in increasing concentrations and sufficiently spaced to avoid any risk of overlapping.

The mass spectrometry image obtained for these various concentrations (FIG. 13A) is normalized for all points in the range using an ROI of identical dimensions, from which a mean reference intensity, or reference signal, for olanzapine is defined. A calibration line (FIG. 13B) can then be plotted, thereafter making it possible during analysis to correlate any signal intensity obtained for olanzapine with a concentration in pmol per mm².

3-Quantification of Olanzapine Using the Mass Spectrometry Image of the Sample

Figure 14A:
FIGS. 14A-14B. Quantification using the mass spectrometry image of the target analyte (olanzapine), in a kidney treated for 2 hours.
Figure 14B:
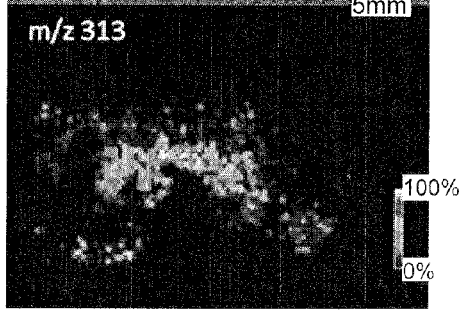

A sagittal section of kidney treated with olanzapine, prepared as specified above and if possible in the same plane as the section used as the control sample during the calculation of the TEC, is deposited on a slide in order to perform an analysis by mass spectrometry imaging (FIG. 14A). A mass spectrometry image of the section of kidney is thus obtained, on which olanzapine is localized through the detection of the m/z 313.3 ion (FIG. 14B) primarily in the medulla.

The signal intensity obtained for olanzapine is normalized in the kidney as a function of the TEC calculated beforehand. This data can then be correlated with the calibration line previously calculated for olanzapine in order to obtain its total concentration in the kidney in pmol/mm².

With knowledge of the thickness and the surface area of the kidney section analyzed it is then possible to determine the quantity of olanzapine in grams per gram of tissue in the sample.

Thus, in the example described herein, a mean concentration of olanzapine (over three experiments) of 41.1 μg/g tissue can be calculated.

We claim:

1. A method for detecting the distribution and quantifying by mass spectrometry imaging at least one target analyte in a tissue sample, comprising the following steps:
 a) depositing the tissue sample containing at least one target analyte on a support for mass spectrometry imaging;
 b) analyzing the tissue sample by mass spectrometry imaging, so as to obtain a mass spectrum signal of said at least one target analyte in said tissue sample;
 c) weighting the signal associated with the mass spectrum of said at least one target analyte in said tissue sample by a tissue extinction coefficient (TEC) specific to each of said at least one target analyte and to the tissue sample, wherein the TEC specific to each of said at least one target analyte is obtained according to the following steps:
depositing a control tissue sample on a support for mass spectrometry imaging;
adding a known concentration of at least one target analyte to a mass spectrometry imaging matrix;
depositing the mixture of said matrix and said at least one target analyte of known concentration on the control tissue sample and said support;
analyzing the control tissue sample by mass spectrometry imaging, so as to obtain a mass spectrum signal of said at least one target analyte both in the control tissue sample and on said support;
and calculating the TEC according to the formula:

$$TEC = \frac{\text{Signal of each of said at least one target analyte on the support}}{\text{Signal of each of said at least one target analyte in the control tissue sample}}$$

or inversely:

$$TEC = \frac{\text{Signal of each of said at least one target analyte in said control tissue sample}}{\text{Signal of each of said at least one target analyte on the support}}$$

wherein said target analyte is optionally isotopically labeled; and
d) using each weighted signal of each of said at least one target analyte to determine the quantity and distribution of each of said at least one target analyte in the tissue sample.

2. The method according to claim 1, wherein the TEC is calculated only once for one of said at least one target analyte in said tissue sample and is reused for each quantification of said at least one target analyte in said tissue sample.

3. The method according to claim 1, wherein said at least one target analyte is a protein, a peptide, a lipid, a metabolite or a small molecule.

4. The method according to claim 1, wherein said at least one target analyte is a protein and an enzymatic and/or chemical pretreatment of said protein is performed prior to detection step b), and wherein detection and quantification are carried out for at least one of the peptides resulting from said pretreatment.

5. The method according to claim 1, wherein the sample is treated with at least one solvent and/or at least one detergent prior to analysis step b).

6. The method according to claim 1, wherein the mass spectrum signal corresponds to the intensity of the peak, the area of the peak or the signal-to-noise ratio of the mass spectrum of at least one target analyte.

7. The method according to claim 1, wherein the signal intensity of the target analyte is weighted directly on the analyzed sample so as to simultaneously visualize the distribution and the concentration of the target analyte in said sample.

8. The method according to claim 1, wherein a known concentration of target analyte labeled with deuterium atoms is added to the tissue sample as an internal standard.

9. The method according to claim 7, wherein a known concentration of target analyte labeled with deuterium atoms is mixed with a matrix before spreading the resulting mixture over the tissue sample.

10. The method according to claim 8, wherein a known concentration of target analyte labeled with deuterium atoms is mixed with a matrix before spreading the resulting mixture over the tissue sample.

11. The method according to claim 1, wherein a matrix is deposited on the tissue sample before analysis step b) and wherein before analysis step b) the homogeneity of the matrix deposition on the sample is evaluated in relation to a deposition of a reference matrix.

12. The method according to claim 1, wherein at least two different target analytes in said sample are detected and quantified simultaneously.

13. The method according to claim 1, wherein the tissue sample is a section of whole animal and wherein the target analyte is detected and quantified by mass spectrometry imaging directly on said section so as to simultaneously compare the distribution of said target in various tissues of the animal.

14. A computer-readable data medium comprising computer-executable instructions suited to enable a computer system to execute step c) of the method according to claim 1.

15. The method according to claim 1, wherein the target analyte is ionizable.

16. The method according to claim 1, wherein a known concentration of target analyte labeled with an isotope is added to the tissue sample as an internal standard.

17. A method for detecting the distribution and quantifying by mass spectrometry imaging at least one target analyte in a tissue sample, comprising the following steps:
a) depositing the tissue sample containing at least one target analyte on a support for mass spectrometry imaging;
b) analyzing the tissue sample by mass spectrometry imaging, so as to obtain a mass spectrum signal of said at least one target analyte in said tissue sample;
c) weighting the signal associated with the mass spectrum of said at least one target analyte in said tissue sample by a tissue extinction coefficient (TEC) specific to each of said at least one target analyte and to the tissue sample, wherein the TEC specific to each of said at least one target analyte is obtained according to the following steps:
depositing a control tissue sample on a support for mass spectrometry imaging;
depositing a known concentration of at least one target analyte on the control tissue sample and the support;
analyzing the control tissue sample by a mass spectrometry imaging technique so as to obtain the mass spectrum of said at least one target analyte in the control tissue sample and on said support;
and calculating the TEC according to the formula:

$$TEC = \frac{\text{Signal of each of said at least one target analyte on the support}}{\text{Signal of each of said at least one target analyte in the control tissue sample}}$$

or inversely:

$$TEC = \frac{\text{Signal of each of said at least one target analyte in said control tissue sample}}{\text{Signal of each of said at least one target analyte on the support}}$$

wherein the target analyte is optionally isotopically labeled; and d) using each weighted signal of each of said at least one target analyte to determine the quantity and distribution of each of said at least one target analyte in the tissue sample.

18. The method according to claim 17, wherein the target analyte is solubilized in a solvent before deposition on the sample and the support, and an evaporation of the solvent is performed before the mass spectrometry imaging analysis.

19. The method according to claim 17, wherein the target analyte is labeled with an isotope.

20. The method according to claim 19, wherein said isotope is deuterium.

* * * * *

UNITED STATES PATENT AND TRADEMARK OFFICE
CERTIFICATE OF CORRECTION

| | | |
|---|---|---|
| PATENT NO. | : 9,182,409 B2 | Page 1 of 1 |
| APPLICATION NO. | : 13/425570 | |
| DATED | : November 10, 2015 | |
| INVENTOR(S) | : Jonathan Stauber et al. | |

It is certified that error appears in the above-identified patent and that said Letters Patent is hereby corrected as shown below:

In The Claims

Column 14,
Line 1, "μm' image" should read --μm$^2$ image--.

Signed and Sealed this
Nineteenth Day of April, 2016

Michelle K. Lee
*Director of the United States Patent and Trademark Office*

UNITED STATES PATENT AND TRADEMARK OFFICE
CERTIFICATE OF CORRECTION

PATENT NO. : 9,182,409 B2
APPLICATION NO. : 13/425570
DATED : November 10, 2015
INVENTOR(S) : Jonathan Stauber et al.

Page 1 of 1

It is certified that error appears in the above-identified patent and that said Letters Patent is hereby corrected as shown below:

In The Claims
Column 9
Line 50, "µm' image" should read --µm² image--.

This certificate supersedes the Certificate of Correction issued April 19, 2016.

Signed and Sealed this
Twenty-third Day of August, 2016

Michelle K. Lee
*Director of the United States Patent and Trademark Office*